United States Patent
Williams

(10) Patent No.: US 7,048,461 B2
(45) Date of Patent: May 23, 2006

(54) BALL JOINT ASSEMBLY WITH WEAR INDICATION

(75) Inventor: Daniel E. Williams, West Lafayette, IN (US)

(73) Assignee: TRW Inc., Lyndhurst, OH (US)

( * ) Notice: Subject to any disclaimer, the term of this patent is extended or adjusted under 35 U.S.C. 154(b) by 0 days.

(21) Appl. No.: 10/251,393

(22) Filed: Sep. 20, 2002

(65) Prior Publication Data

US 2004/0057779 A1 Mar. 25, 2004

(51) Int. Cl.
*F16G 11/00* (2006.01)

(52) U.S. Cl. .................................. 403/27; 403/135
(58) Field of Classification Search ............... 403/29, 403/133, 135, 138, 194
See application file for complete search history.

(56) References Cited

U.S. PATENT DOCUMENTS

| | | | | |
|---|---|---|---|---|
| 3,445,131 A | * | 5/1969 | Gottschald | 403/140 |
| 3,524,664 A | * | 8/1970 | Scheublein, Jr. et al. | 403/140 |
| 3,791,748 A | | 2/1974 | Goodrich, Jr. et al. | 403/27 |
| 3,813,178 A | * | 5/1974 | Herbenar et al. | 403/27 |
| 3,817,640 A | * | 6/1974 | Carter et al. | 403/138 |
| 3,820,907 A | * | 6/1974 | Hassan | 403/27 |
| 3,890,052 A | * | 6/1975 | Herbenar et al. | 403/27 |
| 3,960,457 A | | 6/1976 | Gaines et al. | 403/27 |
| 4,017,197 A | * | 4/1977 | Farrant | 403/27 |
| 4,358,211 A | * | 11/1982 | Goodrich, Jr. et al. | 403/27 |
| 4,576,499 A | | 3/1986 | Smith | 403/27 |
| 4,626,121 A | * | 12/1986 | Tajima et al. | 403/27 |
| 4,679,957 A | | 7/1987 | Bauer | 403/27 |
| 4,749,299 A | * | 6/1988 | Swanson | 403/27 |
| 5,052,844 A | | 10/1991 | Kendall | 403/27 |
| 5,163,769 A | * | 11/1992 | Dresselhouse | 403/27 |
| 6,099,192 A | * | 8/2000 | Free | 403/114 |
| 6,152,637 A | * | 11/2000 | Maughan | 403/27 |
| 6,295,863 B1 | | 10/2001 | Ginder et al. | 73/40 |
| 6,533,491 B1 | * | 3/2003 | Redele | 403/138 |
| 2003/0070476 A1 | * | 4/2003 | Heidemann | |

FOREIGN PATENT DOCUMENTS

| | | | | |
|---|---|---|---|---|
| DE | 3416343 A1 | | 11/1985 | |
| DE | 19546084 | | 5/1997 | |
| FR | 2 833 3121 | * | 6/2003 | |
| JP | 56006911 | | 1/1981 | |
| JP | 358030518 A | * | 2/1983 | 285/27 |
| JP | 358030519 A | * | 2/1983 | 285/27 |
| JP | 358030520 A | * | 2/1983 | 285/27 |
| JP | 361027305 A | * | 2/1986 | 403/132 |
| JP | 362017421 A | * | 1/1987 | 280/511 |
| JP | 362132020 A | * | 6/1987 | 403/27 |
| JP | 362132023 A | * | 6/1987 | 403/27 |
| JP | 362292915 A | * | 12/1987 | 403/27 |
| JP | 362297526 A | * | 12/1987 | 403/27 |
| JP | 63292001 | | 11/1988 | |
| JP | 362293318 A | * | 11/1998 | 403/27 |
| WO | WO01/65130 A1 | | 9/2001 | |

* cited by examiner

*Primary Examiner*—Robert J. Sandy
*Assistant Examiner*—Andre' L. Jackson
(74) *Attorney, Agent, or Firm*—Tarolli, Sunheim, Covell & Tummino L.L.P.

(57) ABSTRACT

A ball joint assembly (10) comprises a socket (12) with a chamber (18), an opening extending through a first axial end (20) of the socket (12), and electrically conductive structure (60) closing the second axial end (22) of the socket (12). An electrically conductive ball stud (30) has a head portion (32) that is received in the chamber (18) and a shank portion (34) that extends through the opening. An electrically conductive bearing member (40) is received in the chamber (18) and provides an electrical connection between the structure (60) and the ball stud (30). An electrically non-conductive biasing member (50) is interposed between the structure (60) and the bearing member (40) and urges the bearing member away from the structure such that, in response to a predetermined amount of wear, the electrical connection between the structure (60) and the ball stud (30) is discontinued.

16 Claims, 4 Drawing Sheets

US 7,048,461 B2

BALL JOINT ASSEMBLY WITH WEAR INDICATION

TECHNICAL FIELD

The present invention relates to a ball joint assembly. More particularly, the present invention relates to a ball joint assembly with structure for indicating wear within the ball joint assembly.

BACKGROUND OF THE INVENTION

A conventional ball joint assembly includes a joint socket, a ball stud, and a bearing. The bearing is supported in a chamber of the joint socket. The bearing supports a head portion of the ball stud within the joint socket. A shank portion of the ball stud extends outwardly of the socket and is rotatable and tiltable relative to the socket.

During use, movement of the head portion of the ball stud on the bearing and relative to the socket results in wear of the bearing within the ball joint assembly. When wear within the ball joint assembly reaches a predetermined amount, the ball joint assembly should be either replaced or repaired.

It is desirable to determine when wear of the predetermined amount occurs within the ball joint assembly. One conventional ball joint assembly that indicates wear includes an electrical contact that is embedded in the bearing. Electrical power is applied to the electrical contact and to the ball stud. When the bearing wears by the predetermined amount, the ball stud engages the electrical contact. When the ball stud engages the electrical contact, an indicator device is energized to indicate wear of the predetermined amount.

In the conventional ball joint assembly, damage to the electrical system may result in failure to indicate wear of the predetermined amount within the ball joint assembly. For example, if a lead wire of the conventional ball joint assembly is severed, the indicator device may not be energized when the ball stud engages the electrical contact. As a result, the conventional ball joint assembly may fail to properly indicate wear of the predetermined amount.

SUMMARY OF THE INVENTION

The present invention relates to a ball joint assembly. The ball joint assembly comprises a socket and an electrically conductive ball stud. The socket includes an internal socket chamber, an opening that extends through a first axial end of the socket and connects to the socket chamber, and electrically conductive structure closing the second axial end of the socket. The ball stud has a head portion that is received in the socket chamber and a shank portion that extends through the opening and outward of the first axial end of the socket. A bearing member is received in the socket chamber and enables the ball stud to tilt relative to the socket. The bearing member is electrically conductive and provides an electrical connection between the structure and the ball stud. An electrically non-conductive biasing member is interposed between the structure and the bearing member. The biasing member urges the bearing member away from the structure such that, in response to a predetermined amount of wear within the ball joint assembly, the electrical connection between the structure and the ball stud is discontinued.

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION OF THE INVENTION

Figure 1:
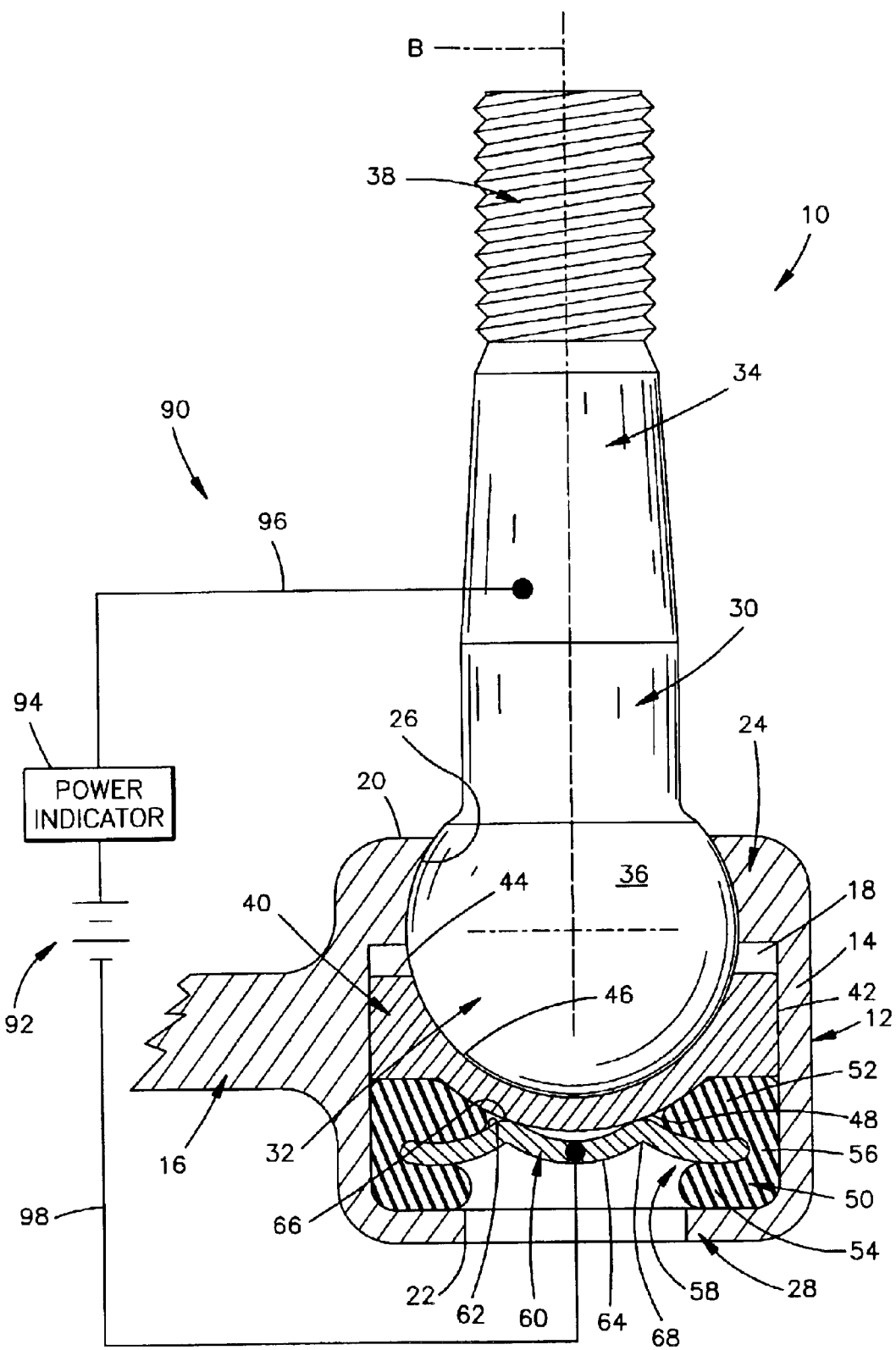
FIG. 1 is an elevation view, partially in section, of a ball joint assembly constructed in accordance with the present invention prior to a predetermined amount of wear within the ball joint assembly.

FIG. 1 is an elevation view, partially in section, of a ball joint assembly 10 constructed in accordance with the present invention. The ball joint assembly 10 includes a housing or socket 12. The socket 12 is formed from an electrically conductive material, such as steel. The socket 12 has a generally cylindrical side wall 14 that is centered on axis A. A mounting flange 16 extends radially outward of the side wall 14 of the socket 12 for mounting of the socket on a piece of equipment. A socket chamber 18 is defined within the side wall 14 of the socket 12.

The socket 12 includes first and second axial ends 20 and 22, respectively. The side wall 14 of the socket 12 at the first axial end 20 is thickened, relative to the remainder of the side wall 14, and forms a first bearing member 24 of the ball joint assembly 10. The first bearing member 24 includes an annular, curvilinear bearing surface 26 that narrows toward the first axial end 20 of the socket 12. The bearing surface 26 is a smooth, low friction surface.

The second axial end 22 of the socket 12 includes a cylindrical opening (not shown) that is defined within the side wall 14. After assembly of the ball joint assembly 10, as will be described below, the side wall 14 adjacent the second axial end 22 of the socket 12 is bent radially inwardly to form a radially inwardly bent portion 28 of the socket 12.

The ball joint assembly 10 also includes a ball stud 30. The ball stud 30 is formed from an electrically conductive material, such as steel. The ball stud 30 includes a head portion 32 and a shank portion 34. The head portion 32 of the ball stud 30 illustrated in FIG. 1 is spherical and is defined by a smooth outer surface 36. The shank portion 34 of the ball stud 30 extends axially along axis B from the ball stud. FIG. 1 illustrates axis A and axis B being coaxial. In the assembled ball joint assembly 10, axis B is rotatable and tiltable relative to axis A. An end 38 of the shank portion 34 of the ball stud 30 opposite the head portion 32 may be threaded.

A second bearing member 40 of the ball joint assembly 10 is formed from an electrically conductive material, such as steel. The second bearing member 40 includes a cylindrical outer surface 42, an upper surface 44 that includes a semi-spherical bearing surface 46, and a lower surface 48 that is domed. The semi-spherical bearing surface 46 of the second bearing member 40 is a low friction surface.

The ball joint assembly 10 also includes an electrically non-conductive spring/seal element 50. The spring/seal element 50 is formed from a resilient material, such as rubber. The spring/seal element 50 has a generally U-shaped cross-sectional shape that includes upper and lower wall portions 52 and 54, respectively, and an outer wall portion 56 that interconnects the upper and lower wall portions. An annular groove 58 is formed in the spring/seal element 50 between the upper and lower wall portions 52 and 54. The outer wall portion 56 of the spring/seal member 50 defines a radially outer end of the annular groove 58. As an alternative to the spring/seal element 50, an electrically non-conductive spring and a separate electrically non-conductive seal may be used.

The ball joint assembly 10 also includes a cover member 60 for closing the second axial end 22 of the socket 12. The cover member 60 is formed from an electrically conductive material, such as steel. The cover member 60 is disk-shaped and includes upper and lower surfaces 62 and 64, respectively. The upper surface 62 includes an annular protruding portion 66 that extends axially outwardly of the remainder of the upper surface 62. The lower surface 64 includes an annular recessed portion 68 at a location corresponding to the annular protruding portion 66 on the upper surface 62.

According to an exemplary method of assembling the ball joint assembly 10 of the present invention, the shank portion 34 of the ball stud 30 is inserted through the opening at the second axial end 22 of the socket 12, through the socket chamber 18, and outward through the opening on the first axial end 20 of the socket 12 so that the ball head 32 of the ball stud 30 rests on the curvilinear bearing surface 26 of the first bearing member 24. The second bearing member 40 is then inserted through the opening on the second axial end 22 of the socket 12 and is positioned so that the semi-spherical bearing surface 46 of the second bearing member 40 contacts the smooth outer surface 36 of the ball head 32.

The cover member 60 is positioned in the annular groove 58 of the spring/seal element 50 so that the upper wall portion 52 of the spring/seal element overlies the periphery of the upper surface 62 of the cover member, the lower wall portion 54 of the spring/seal element overlies the periphery of the lower surface 64 of the cover member, and the outer wall portion 56 of the spring/seal element radially surrounds the cover member. The spring/seal element 50 electrically insulates the periphery of the cover member 60.

The spring/seal element 50 and cover member 60 are then inserted through the opening on the second axial end 22 of the socket 12 such that the upper wall portion 52 of the spring/seal element 50 contacts the lower surface 48 of the second bearing member 40. The side wall 14 of the second axial end 22 of the socket 12 is then bent radially inwardly to form the radially inwardly bent portion 28. The radially inwardly bent portion 28 applies a predetermined load on the spring/seal element 50 and axially deforms the spring/seal element so that the annular protruding portion 66 of the upper surface 62 of the cover member 60 contacts the lower surface 48 of the second bearing member 40, as shown in FIG. 1. The axially deformed spring/seal element 50 urges the second bearing member 40 toward the first axial end 20 of the socket 12. Additionally, the axially deformed spring/seal element 50 seals between the cover member and the socket 12 for preventing contaminants from entering the socket chamber 18 through the second axial end 22 of the socket.

The ball joint assembly 10 of the present invention advantageously compensates for wear within the ball joint assembly 10. Specifically, the ball joint assembly 10 of the present invention compensates for wear of the first and second bearing members 24 and 40. To compensate for wear of the second bearing member 40, the axially compressed spring/seal element 50 urges the second bearing member 40 against the head portion 32 of the ball stud 30. To compensate for wear of the first bearing member 24, the axially compressed spring/seal element 50 urges both the second bearing member 40 and the head portion 32 of the ball stud 30 toward the first bearing member 24.

Figure 2:
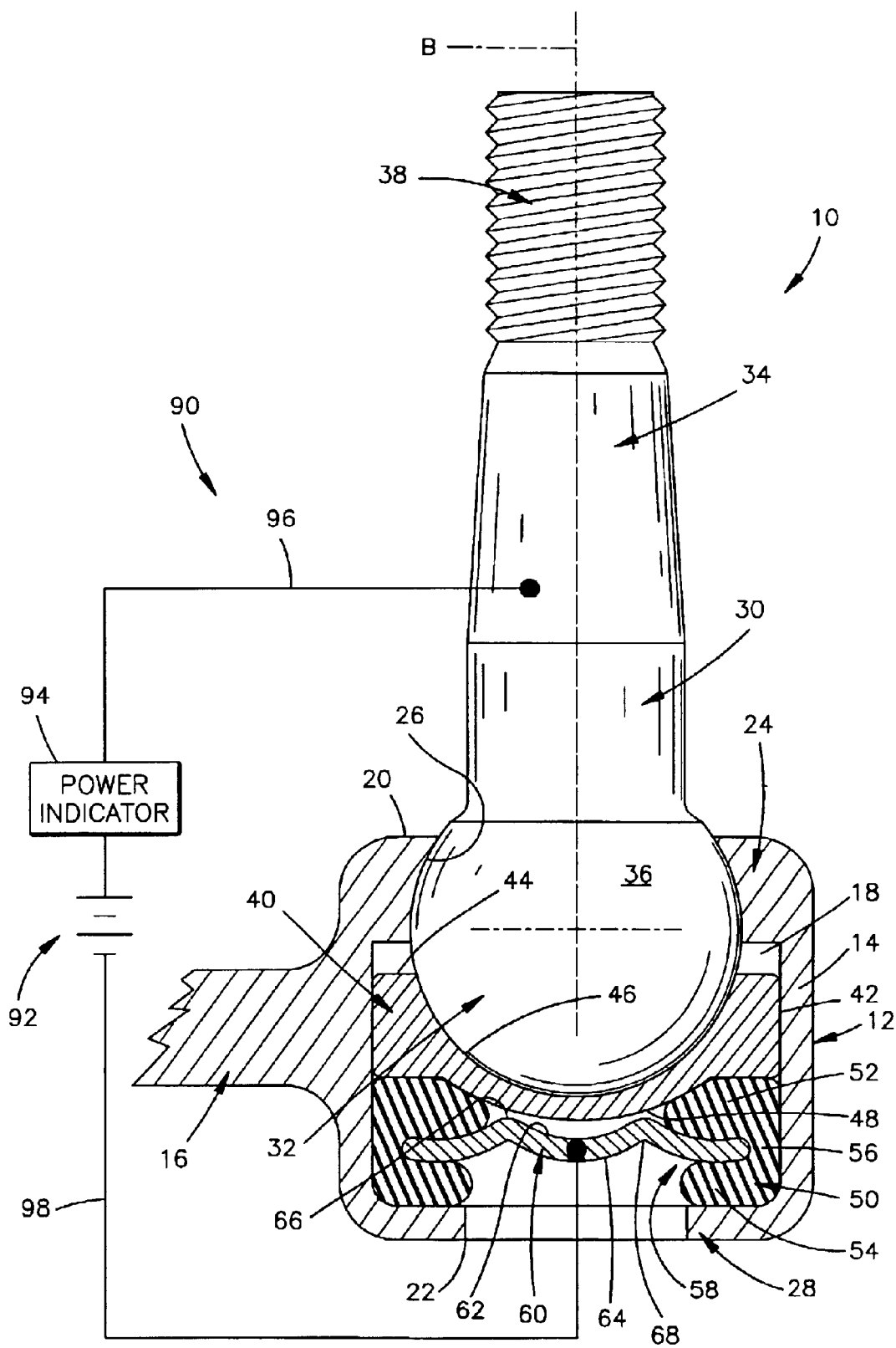
FIG. 2 illustrates the ball joint assembly of FIG. 1 after a predetermined amount of wear within the ball joint assembly.

Additionally, the ball joint assembly 10 of the present invention may be used in a system, indicated by 90 in FIGS. 1 and 2, for determining when a predetermined amount of wear within the ball joint assembly 10 has occurred. The wear determining system 90 includes an electric power source 92 and a power indicator 94. The electric power source 92 includes first and second leads 96 and 98, respectively. The power indicator 94 indicates when power is transferred between the first and second leads 96 and 98. The electric power source 92 and the power indicator 94 may be included in the form of a probe that may be used for determining wear of the ball joint assembly 10.

When the cover member 60 contacts the second bearing member 40, as shown in FIG. 1, and the first lead 96 of the electric power source 92 is applied to the shank portion 34 of the ball stud 30 and the second lead 98 is applied to the electrically conductive cover member 60, the power indicator 94 indicates electrical power passing through the ball joint assembly 10. When electrical power passes through the ball joint assembly 10, the wear within the ball joint assembly is considered to be less than the predetermined amount. By connecting the second lead 98 to the cover member 60 of the ball joint assembly 10, there is no need to provide a seal around the second lead 98 as the second lead does not extend into the socket chamber 18 of the ball joint assembly 10.

As the ball joint assembly 10 wears, the spring/seal element 50 urges the second bearing member 40 away from the cover member 60. When wear within the ball joint assembly increases beyond the predetermined amount, the spring/seal element 50 urges the second bearing member 40 away from the cover member 60 and contact between the second bearing member 40 and the cover member 60 discontinues, as is shown in FIG. 2.

When the cover member 60 is spaced away or electrically separated from the second bearing member 40, as shown in FIG. 2, and the first lead 96 of the electric power source 92 is applied to the shank portion 34 of the ball stud 30 and the second lead 98 is applied to the cover member 60, the power indicator 94 indicates no electrical power passing through the ball joint assembly 10. When no electrical power passes through the ball joint assembly 10, the wear within the ball joint assembly 10 is considered to be greater than the predetermined amount. Moreover, wear to the system 90 that results in the power indicator 94 not receiving electrical power will indicate the need for replacement or repair.

Thus, when included in the wear determining system 90, the ball joint assembly 10 acts as a normally closed switch. The ball stud 30 acts as a first electrical contact, the cover member 60 acts as a second electrical contact, and the second bearing member 40 acts as a switch member in the normally closed switch. When the wear within the ball joint assembly 10 is less than the predetermined amount, the switch remains closed. The switch opens in response to the wear within the ball joint assembly 10 exceeding the predetermined amount.

Figure 3:
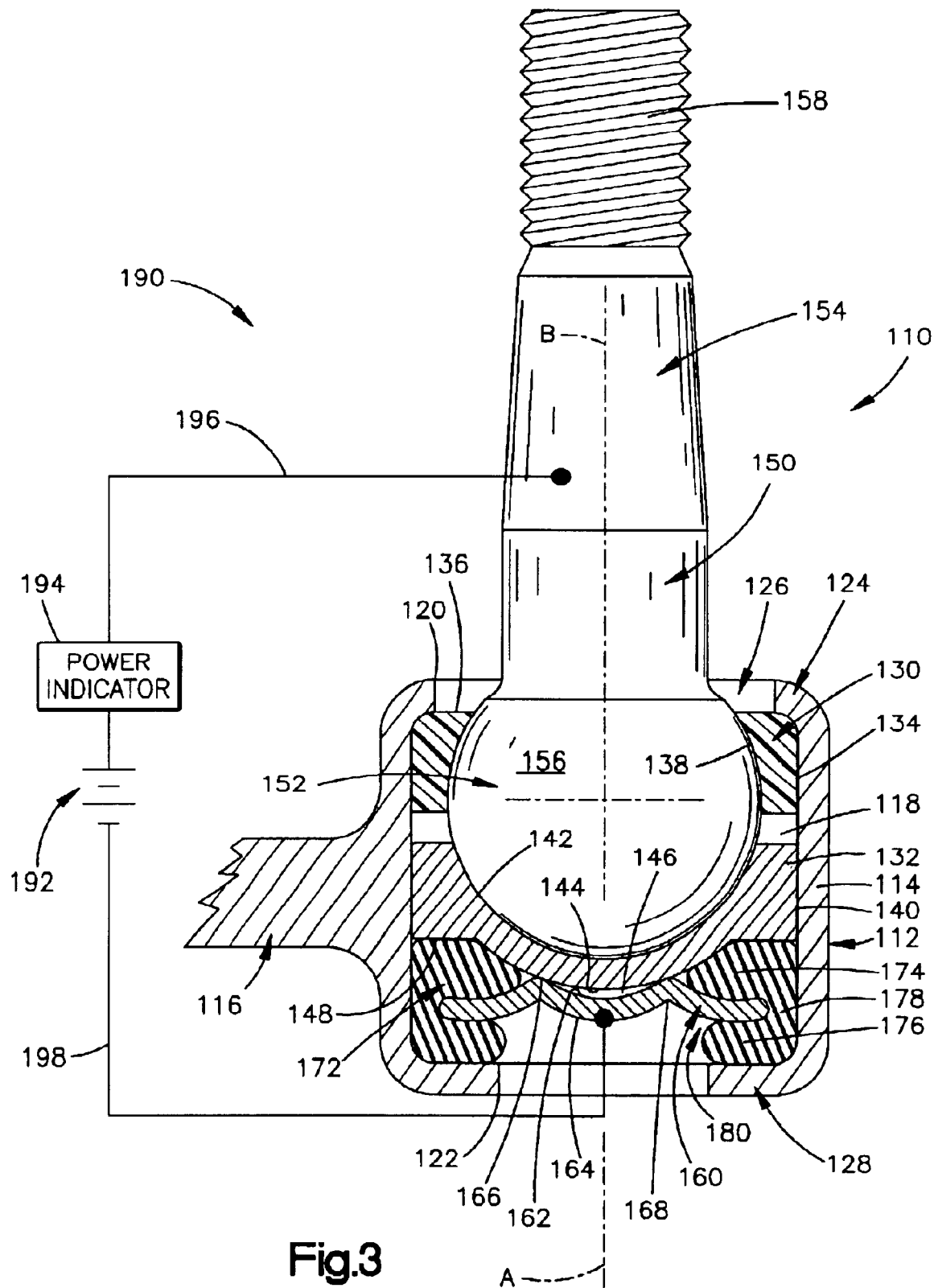
FIG. 3 is an elevation view, partially in section, of a ball joint assembly constructed in accordance with a second embodiment of the present invention prior to a predetermined amount of wear within the ball joint assembly.

FIG. 3 is an elevation view, partially in section, of a ball joint assembly 110 constructed in accordance with a second embodiment of the present invention prior to a predetermined amount of wear within the ball joint assembly. The ball joint assembly 110 includes a socket 112 that is formed from an electrically conductive material, such as steel. The socket 112 has a generally cylindrical side wall 114 that is centered on axis A. A mounting flange 116 extends radially outward of the side wall 114 of the socket 112 for mounting of the socket on a piece of equipment. A socket chamber 118 is defined within the side wall 114 of the socket 112.

The socket 112 includes first and second axial ends 120 and 122, respectively. The side wall 114 of the socket 112 includes a first radially inwardly bent portion 124 adjacent the first axial end 120 of the socket 112. The first radially inwardly bent portion 124 defines an opening 126 at the first axial end 120 of the socket 112. The second axial end 122 of the socket 112 includes a cylindrical opening (not shown) that is defined within the side wall 114. After assembly of the ball joint assembly 110, as will be described below, the side wall 114 adjacent the second axial end 122 of the socket 112 is bent radially inwardly to form a second radially inwardly bent portion 128 of the socket 112.

The socket 112 illustrated in FIG. 3 also includes first and second bearing members 130 and 132, respectively. The first bearing member 130 is annular and is sized to fit within the socket chamber 118. Preferably, the first bearing member 130 is formed from a low friction material, such as plastic. The first bearing member 130 includes an outer wall 134 that fits snugly against the side wall 114 of the socket 112 and an end wall 136 for resting against the first radially inwardly bent portion 124 of the socket 112. A curvilinear bearing surface 138 of the first bearing member 130 defines an internal channel through the first bearing member 130 that narrows toward end wall 136.

The second bearing member 132 is formed from an electrically conductive material, such as steel. The second bearing member 132 includes a cylindrical outer surface 140, a semi-spherical bearing surface 142 that is a low friction surface, and an outer surface 144 that includes a central domed portion 146 and an annular rim portion 148.

The ball joint assembly 110 also includes a ball stud 150. The ball stud 150 is formed from an electrically conductive material, such as steel. The ball stud 150 includes a head portion 152 and a shank portion 154. The head portion 152 of the ball stud 150 illustrated in FIG. 3 is spherical and is defined by a smooth outer surface 156. The shank portion 154 of the ball stud 150 extends axially along axis B of the ball stud. FIG. 3 illustrates axis A and axis B as being coaxial. In the assembled ball joint assembly 110, axis B is rotatable and tiltable relative to axis A. An end 158 of the shank portion 154 of the ball stud 150 opposite the head portion 152 is threaded.

The ball joint assembly 110 also includes a cover member 160 for closing the second axial end 122 of the socket 112. The cover member 160 is formed from an electrically conductive material, such as steel. The cover member 160 is disk-shaped and includes upper and lower surfaces 162 and 164, respectively. The upper surface 162 includes an annular protruding portion 166 that extends axially outwardly of the remainder of the upper surface 162. The lower surface 164 includes an annular recessed portion 168 at a location corresponding to the annular protruding portion 166 on the upper surface 162.

An electrically non-conductive spring/seal element 172 for the ball joint assembly 110 is formed from a resilient material, such as rubber. The spring/seal element 172 has a generally U-shaped cross-sectional shape that includes upper and lower wall portions 174 and 176, respectively, and an outer wall portion 178 that interconnects the upper and lower wall portions. An annular groove 180 is formed in the spring/seal element 172 between the upper and lower wall portions 174 and 176. The outer wall portion 178 of the spring/seal member 178 defines a radially outer end of the annular groove 180. As an alternative to the spring/seal element 160, an electrically non-conductive spring and a separate electrically non-conductive seal may be used.

According to an exemplary method of assembling the ball joint assembly 110 of the present invention, the first bearing member 130 is inserted into the socket chamber 118 through the opening on the second axial end 122 of the socket 112. The first bearing member 130 is pressed toward the first axial end 120 of the socket 112 until the end wall 136 of the first bearing member 130 rests against the first radially inwardly bent portion 124 of the socket 112. The shank portion 154 of the ball stud 150 is then inserted through the opening at the second axial end 122 of the socket 112, through the socket chamber 118, and outward through the opening 126 on the first axial end 120 of the socket 112 so that the head portion 152 of the ball stud 150 rests on the curvilinear bearing surface 138 of the first bearing member 130. The second bearing member 132 is then inserted through the opening on the second axial end 122 of the socket 112 and positioned so that the semi-spherical bearing surface 142 of the second bearing member 132 contacts the smooth outer surface 156 of the head portion 152 of the ball stud 150.

The cover member 160 is positioned in the annular groove 180 of the spring/seal element 172 so that the upper wall portion 174 of the spring/seal element overlies the periphery of the upper surface 162 of the cover member, the lower wall portion 176 of the spring/seal element overlies the periphery of the lower surface 164 of the cover member, and the outer wall portion 178 of the spring/seal element radially surrounds the cover member. The spring/seal element 172 electrically insulates the periphery of the cover member 160.

The spring/seal element 172 and cover member 160 are then inserted through the opening on the second axial end 122 of the socket 112 such that the upper wall portion 174 of the spring/seal element 172 contacts the outer surface 144 of the second bearing member 132. The second axial end 122 of the socket 112 is then bent radially inwardly to form the second radially inwardly bent portion 128. The second radially inwardly bent portion 128 applies a predetermined load on the spring/seal element 172 to axially deform the spring/seal element. The annular protrusion 170 of the cover member 160 contacts the second bearing member 132 when the spring/seal element 172 is deformed axially, as shown in FIG. 3. The spring/seal element 172, when deformed axially, urges the second bearing member 132 toward the first axial end 120 of the socket 112 and also creates a seal between the second radially inwardly bent portion 128 of the socket 112 and the cover member 160 for preventing contaminants from entering the socket 112.

The ball joint assembly 110 of FIG. 3 also compensates for wear within the ball joint assembly. To compensate for wear of the second bearing member 132, the axially compressed spring/seal element 172 urges the second bearing member 132 against the head portion 152 of the ball stud 150. To compensate for wear of the first bearing member 130, the axially compressed spring/seal element 172 urges both the second bearing member 132 and the head portion 152 of the ball stud 150 toward the first bearing member 130.

Similarly to the ball joint assembly 10 of FIG. 1, the ball joint assembly 110 of FIG. 3 may be used in a system 190 for determining when a predetermined amount of wear within the ball joint assembly 110 has occurred. The wear determining system 190 includes an electric power source 192 and a power indicator 194. The electric power source 192 includes first and second lead wires 196 and 198, respectively. The power indicator 194 indicates when power is transferred between the first and second lead wires 196 and 198. The wear determining system 190, including the electric power source 192 and the power indicator 194, may be included in the form of a probe that may be used for determining wear of the ball joint assembly.

When the cover member 160 contacts the second bearing member 132, as shown in FIG. 3, and the first lead wire 196 of the electric power source 192 is applied to the shank portion 154 of the ball stud 150 and the second lead 198 is applied to the cover member 160, the power indicator 194 indicates electrical power passing through the ball joint assembly 110. When electrical power passes through the ball joint assembly 110, the wear within the ball joint assembly 110 is considered to be less than the predetermined amount.

Figure 4:
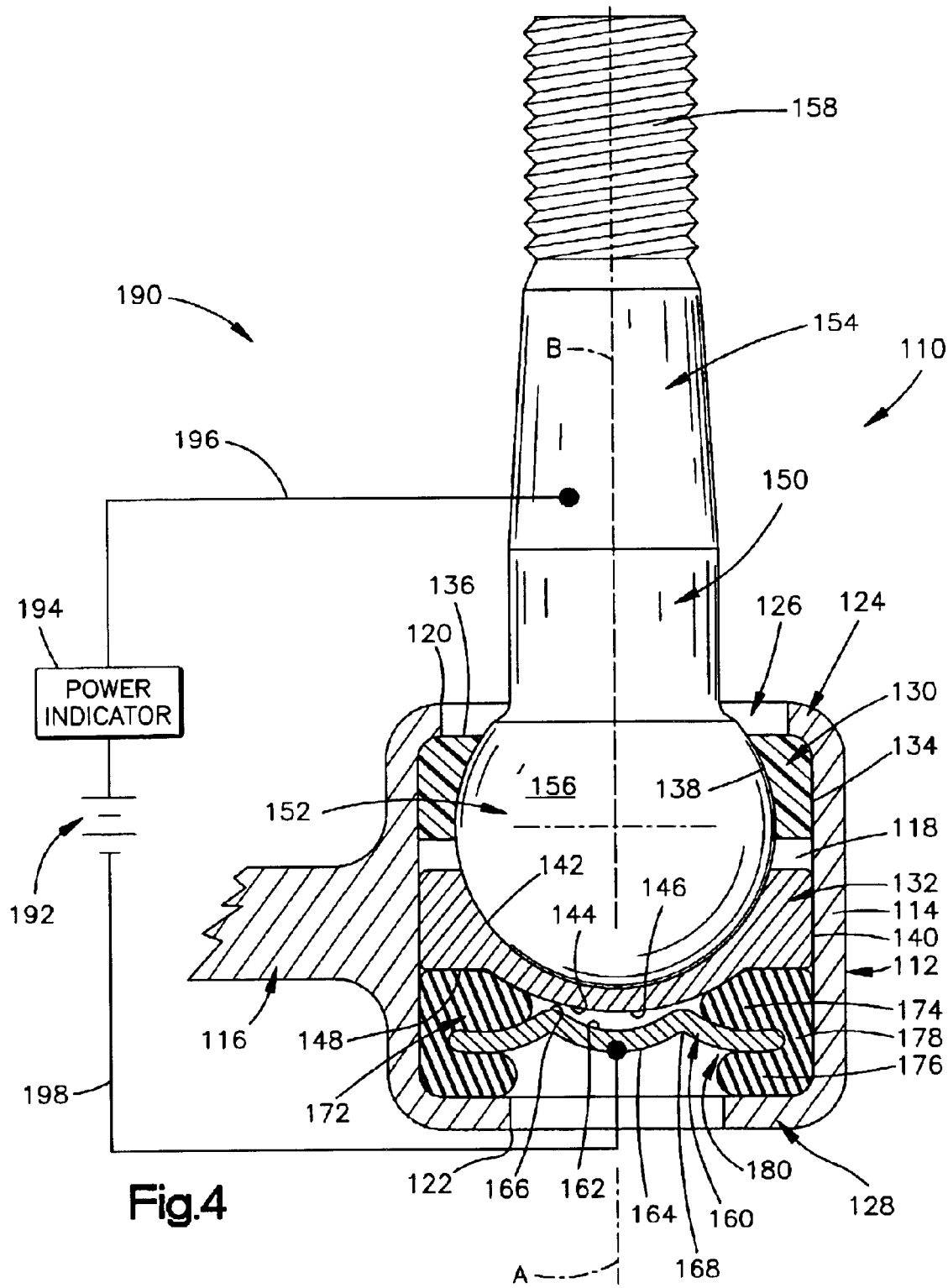
FIG. 4 illustrates the ball joint assembly of FIG. 3 after a predetermined amount of wear within the ball joint assembly.

As the ball joint assembly 110 wears, the spring/seal element 172 biases the second bearing member 132 away from the cover member 160. When wear increases beyond the predetermined amount, contact between the second bearing member 132 and the cover member 160 discontinues. FIG. 4 illustrates the ball joint assembly 110 after wear beyond the predetermined amount.

When the cover member 160 is spaced away from the second bearing member 132, as shown in FIG. 4, and the first lead wire 196 of the electric power source 192 is applied to the shank portion 154 of the ball stud 150 and the second lead wire 198 is applied to the cover member 160, the power indicator 194 indicates no electrical power passing through the ball joint assembly 110. When no electrical power passes through the ball joint assembly 110, the wear within the ball joint assembly 110 is considered to be greater than the predetermined amount.

Thus, when included in the wear determining system 190, the ball joint assembly 110 acts as a normally closed switch. The cover member 160 acts as one electrical contact, and the ball stud 150 acts as another electrical contact, and the second bearing member 132 acts as a switch member in the normally closed switch.

From the above description of the invention, those skilled in the art will perceive improvements, changes and modifications. For example, the socket 112 of FIG. 3 may be closed at the second axial end 122 and the ball joint assembly 110 may be assembly through the opening 126 at the first axial end 120 of the socket 112 prior to forming of the first radially inwardly bent portion 124. In such an embodiment, the second bearing member is preferably electrically insulated from the socket. Such improvements, changes and modifications within the skill of the art are intended to be covered by the appended claims.

What is claimed is:

1. A ball joint assembly comprising:
a socket including an internal socket chamber, an opening that extends through a first axial end of the socket and connects to the socket chamber;
an electrically conductive structure closing the second axial end of the socket;
an electrically conductive ball stud having a head portion received in the socket chamber and a shank portion extending through the opening and outward of the first axial end of the socket;
a bearing member received in the socket chamber and enabling the ball stud to tilt relative to the socket, the bearing member being electrically conductive and providing an electrical connection between the structure and the ball stud; and
an electrically non-conductive biasing member interposed between the structure and the bearing member, the biasing member urging the bearing member away from the structure such that, in response to a predetermined amount of wear within the ball joint assembly, the electrical connection between the structure and the ball stud is discontinued, the electrically conductive structure is electrically insulated from the socket when the electrical connection between the structure and the ball stud is discontinued.

2. The ball joint assembly of claim 1 wherein the bearing member includes a domed portion that extends toward the second axial end of the socket, the structure includes a protruding portion that extends toward the first axial end of the socket, the bearing member providing an electrical connection between the structure and the ball stud when the domed portion of the bearing member and the protruding portion of the structure are in electrical contact.

3. The ball joint assembly of claim 1 wherein the ball stud forms a first electrical contact of a normally closed switch, the structure forms a second electrical contact of the normally closed switch, and the bearing member forms a switch member of the normally closed switch, the biasing member electrically separating the switch member from at least one of the first and second electrical contacts to open the normally closed switch when wear within the ball joint assembly exceeds the predetermined amount.

4. The ball joint assembly of claim 1 wherein the electrically conductive structure includes a cover member that is received in the socket chamber for closing the second axial end of the socket.

5. The ball joint assembly of claim 4 further including a seal for sealing between the socket and the cover member for preventing contaminants from entering the socket chamber through the second axial end of the socket.

6. The ball joint assembly of claim 4 wherein the biasing member receives the cover member and surrounds the cover member to electrically insulate the cover member from the socket when the electrical connection between the structure and the ball stud is discontinued.

7. The ball joint assembly of claim 6 wherein the biasing member also forms a seal for sealing between the cover member and the socket for preventing contaminants from entering the socket chamber through the second axial end of the socket.

8. A ball joint assembly comprising:
a housing,
a ball stud having a head portion at least partially enclosed by said housing and a shank portion extending away from said housing, said ball stud being formed of an electrically conductive material,
a bearing assembly disposed in said housing to urge said ball stud and a bearing surface into abutting engagement, said head end portion of said ball stud being movable relative to said bearing surface, said bearing assembly includes a first member formed of an electrically nonconductive material and a second member formed of an electrically conductive material, said second member is supported in said bearing assembly by said first member and said first member is effective to electrically insulate said second member from said ball stud when said second member and said ball stud are in the second condition,
said second member and said ball stud being relatively movable from a first condition to a second condition in response to wear of at least one component of said ball joint assembly, said second member and said ball stud being electrically interconnected when said second member and said ball stud are in the first condition, said second member and said ball stud being electrically disconnected when said second member and said ball stud are in the second condition to thereby provide an indication of the occurrence of wear in the ball joint assembly.

9. A ball joint assembly as set forth in claim 8 wherein said first and second members cooperate to at least partially to block movement of contaminants into a portion of said housing in which said head portion of said ball stud is disposed.

10. A ball joint assembly as set forth in claim 8 wherein said second member is disposed adjacent to one end portion of said housing and is effective to urge said head portion of said ball stud toward an end portion of said housing opposite from said one end portion of said housing.

11. A ball joint assembly comprising:

a housing, a ball stud having a head portion at least partially enclosed by said housing and a shank portion extending away from said housing, said ball stud being formed of an electrically conductive material, a bearing assembly disposed in said housing to urge said ball stud and a bearing surface into abutting engagement, said head end portion of said ball stud being movable relative to said bearing surface, said bearing assembly includes a first member formed of an electrically nonconductive material and a second member formed of an electrically conductive material, said bearing assembly includes a bearing member formed of an electrically conductive material and disposed in engagement with said head portion of said ball stud, said first member in said bearing assembly being effective to press said bearing member against said head portion of said ball stud, said second member and said ball stud being relatively movable from a first condition to a second condition in response to wear of at least one component of said ball joint assembly, said second member and said ball stud being electrically interconnected when said second member and said ball stud are in the first condition, said second member and said ball stud being electrically disconnected when said second member and said ball stud are in the second condition to thereby provide an indication of the occurrence of wear in the ball joint assembly.

12. A ball joint assembly as set forth in claim 11 wherein said second member in said bearing assembly is disposed in engagement with said bearing member when said second member and said ball stud are in the first condition, said second member being spaced from said bearing member when said second member and said ball stud are in the second condition.

13. A ball joint assembly comprising a housing, a ball stud having a head end portion which is at least partially enclosed by and is movable relative to said housing, said head end portion of said ball stud being movable relative to said housing from a first position to a second position upon occurrence of a predetermined amount of wear in said ball joint assembly, and an electrical contact arrangement which is operable from a first condition to a second condition upon movement of said ball stud relative to said housing from the first position to the second position, said electrical contact arrangement being closed enabling an electrical circuit to be completed when said electrical contact arrangement is in the first condition, said electrical contact arrangement being open to interrupt the electrical circuit when said electrical contact arrangement is in the second condition.

14. A ball joint assembly comprising:

a housing, a ball stud having a head portion at least partially enclosed by said housing and a shank portion extending away from said housing, said ball stud being formed of an electrically conductive material, a bearing assembly disposed in said housing to urge said ball stud and a bearing surface into abutting engagement, said head end portion of said ball stud being movable relative to said bearing surface, said bearing assembly includes a first member formed of an electrically nonconductive material and a second member formed of an electrically conductive material, said first member has a central opening, said second member and said ball stud being relatively movable from a first condition to a second condition in response to wear of at least one component of said ball joint assembly, said second member and said ball stud being electrically interconnected when said second member and said ball stud are in the first condition, said second member extends across said central opening in said first member and makes contact with an electrically conductive component of said ball joint assembly at a location adjacent to the central opening when said second member and said ball stud are in the first condition, said second member and said ball stud being electrically disconnected when said second member and said ball stud are in the second condition to thereby provide an indication of the occurrence of wear in the ball joint assembly.

15. A ball joint assembly comprising:

a housing, a ball stud having a head end portion which is at least partially enclosed by and is movable relative to said housing, said head end portion of said ball stud being movable relative to said housing from a first position to a second position upon occurrence of a predetermined amount of wear, and an electrical circuit responsive to the predetermined amount of wear of at least one part of said ball joint, said electrical circuit being closed and being effective to conduct electrical current prior to said predetermined amount of wear and opened to interrupt the electrical circuit and to interrupt the flow of electrical current in response to said predetermined amount of wear, said electrical circuit includes an electrical contact arrangement which is operable from a first condition to a second condition upon movement of said ball stud relative to said housing from the first position to the second position, said electrical contact arrangement being closed enabling an electrical circuit to be completed when said electrical contact arrangement is in the first condition, said electrical contact arrangement being open to interrupt the electrical circuit when said electrical contact arrangement is in the second condition.

16. A ball joint assembly comprising:

a housing, a bal stud having a head end portion which is at least partially enclosed by and is movable relative to said housing, and an electrical circuit responsive to a predetermined amount of wear of at least one part of said ball joint, said electrical circuit being closed and being effective to conduct electrical current prior to said predetermined amount of wear and opened to interrupt the electrical circuit and to interrupt the flow of electrical current in response to said predetermined amount of wear, said electrical circuit includes said head end portion of said ball stud and a contact member, said head end portion of said ball stud and said contact member being relatively movable upon the occurrence of the predetermined amount of wear to interrupt the electrical circuit.

* * * * *

UNITED STATES PATENT AND TRADEMARK OFFICE
CERTIFICATE OF CORRECTION

PATENT NO. : 7,048,461 B2
APPLICATION NO. : 10/251393
DATED : May 23, 2006
INVENTOR(S) : Daniel E. Williams It is certified that error appears in the above-identified patent and that said Letters Patent is hereby corrected as shown below:

Column 9 delete lines 55-67.
    Column 10 delete lines 1-6.
    Column 10 line 65 before "stud" delete "bal" and insert --ball--

Signed and Sealed this

Eighth Day of April, 2008

JON W. DUDAS
*Director of the United States Patent and Trademark Office*